United States Patent
Belloni et al.

(10) Patent No.: US 6,828,337 B2
(45) Date of Patent: Dec. 7, 2004

(54) SELECTIVE RETINOID AGONISTS

(75) Inventors: Paula Nanette Belloni, Half Moon Bay, CA (US); Michael Klaus, Weil am Rhein (DE); Jean-Marc Lapierre, Mountain View, CA (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/323,306

(22) Filed: Dec. 19, 2002

(65) Prior Publication Data

US 2003/0176726 A1 Sep. 18, 2003

Related U.S. Application Data

(62) Division of application No. 09/625,806, filed on Jul. 26, 2000, now Pat. No. 6,528,677.

(30) Foreign Application Priority Data

Aug. 2, 1999 (EP) .............................. 99115223

(51) Int. Cl.$^7$ .................. A61K 31/44; A61K 31/21; A61K 31/215; C07D 213/02; C07D 307/93
(52) U.S. Cl. ................ 514/350; 514/350; 514/351; 514/354; 514/352; 514/506; 514/529; 514/356; 546/193; 549/465
(58) Field of Search ................. 514/350, 351, 514/354, 506, 529, 352, 356; 546/193; 549/465

(56) References Cited

FOREIGN PATENT DOCUMENTS

| WO | WO 92/06948 | 4/1992 |
| WO | WO 99/33821 | 8/1999 |

OTHER PUBLICATIONS

Caplus, 96:104006, English Abstract, Guzman, A. et al., Synthesis, 1981, vol. 12, pp. 989–991, 12/81.

*Primary Examiner*—Cecilia Tsang
*Assistant Examiner*—Taylor V. Oh
(74) *Attorney, Agent, or Firm*—George W. Johnston; Dennis P. Tramaloni; Eileen M. Ebel

(57) ABSTRACT

This invention relates to new RAR selective retinoid agonists of formula I

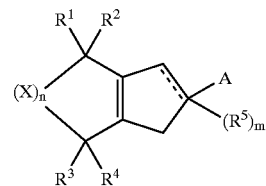

wherein the symbols are as defined in the specification to their pharmaceutically acceptable salts, individual isomers or to a racemic or non-racemic mixture; to pharmaceutical compositions containing them, and to methods for their use as therapeutic agents.

13 Claims, No Drawings

SELECTIVE RETINOID AGONISTS

CONTINUITY INFORMATION

This application is a Divisional of Ser. No. 09/625,806, filed Jul. 26, 2000, now U.S. Pat. No. 6,528,677.

FIELD OF THE INVENTION

This invention relates to new RAR selective retinoid agonists, to the use of such retinoic acid receptor agonists, particularly retinoic acid receptor γ (RARγ) selective agonists for the treatment of emphysema.

BACKGROUND OF THE INVENTION

Chronic obstructive pulmonary disease (COPD) is a major cause of morbidity and mortality, ranking third and fourth as the leading cause of death in the European Union and North America respectively. COPD is characterized by reduced maximum expiratory flow, which does not change over several months and which persists for 2 or more consecutive years. Patients with the most severe form of COPD generally present with a significant degree of emphysema. Emphysema is defined anatomically by permanent airspace enlargement distal to the terminal bronchioles. It is characterized by gradual loss of lung recoil, alveolar destruction, decreased alveolar surface area and gas exchange, leading to a reduced FEV1. These two features, impaired gas exchange and reduction in expiratory flow, are characteristic physiological abnormalities from which patients with emphysema suffer. The main symptom of patients with severe emphysema is shortness of breath during minimal physical activity.

The most common cause of emphysema is cigarette smoking although other potential environmental toxins may also contribute. These various insulting agents activate destructive processes in the lung including release of active proteases and free radical oxidants in excess of protective mechanisms. The imbalance in protease/anti-protease levels leads to destruction of the elastin matrix, loss of elastic recoil, tissue damage and continuous decline in lung function. Removing the injurious agents (i.e. quit smoking) slows the rate of damage, however, the damaged alveolar structures do not repair and lung function is not regained.

Retinoic acid is a multifunctional modulator of cellular behavior, having the potential to alter both extracellular matrix metabolism and normal epithelial differentiation. In lung, retinoic acid has been shown to modulate various aspects of lung differentiation by interacting with specific retinoic acid receptors (RAR) that are selectively expressed temporally and spatially. Coordinated activation of RARβ and RARγ has been associated with lung branching and alveolization/septation. During alveolar septation, retinoic acid storage granules increase in the fibroblastic mesenchyme surrounding alveolar walls and RARγ expression in the lung peaks. Depletion of these retinyl-ester stores parallels the deposition of new elastin matrix and septation. In support of this concept, (Massaro et al., Am. J. Physiol., 1996, 270, L305–L310) demonstrated that postnatal administration of retinoic acid increases the number of alveoli in rats. Furthermore, the capacity of dexamethasone to prevent the expression of CRBP and RARβ mRNA and subsequent alveolar septation in developing rat lungs was abrogated by all-trans retinoic acid.

Recent studies demonstrated that all-trans retinoic acid can induce formation of new alveoli and return elastic recoil to near normal in animal models of emphysema (D. Massaro et al. Nature Medicine, 1997, 3, 675). However, the mechanism by which this occurs remains unclear.

Retinoids are a class of compounds structurally related to vitamin A, comprising natural and synthetic compounds. Several series of retinoids have been found clinically useful in the treatment of dermatological and oncological diseases. Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lungs. Retinoids exert their biological effects through a series of hormone nuclear receptors that are ligand inducible transcription factors belonging to the steroid/thyroid receptor superfamily. The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand.

In many non-pulmonary tissues, retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis. A limitation in the therapeutic use of retinoids outside of cancer has stemmed from the relative toxicity observed with the naturally occurring retinoids, all-trans retinoic acid and 9-cis retinoic acid. These natural ligands are non-selective and therefore have pleiotropic effects throughout the body, which are often toxic. Recently various retinoids have been described that interact selectively or specifically with the RAR or RXR receptors or with specific subtypes (α, β, γ) within a class.

SUMMARY OF THE INVENTION

In one aspect, this invention provides new RAR selective retinoid agonists of formula I

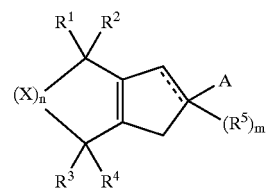

I wherein
the dotted bond is either present and forms a double bond, or is absent;
R$^1$, R$^2$, R$^3$, R$^4$ are independently of each other hydrogen or alkyl;
X is R$^8$R$^9$C< for n=1, 2 or 3; or
X is oxygen for n=1;
R$^8$ and R$^9$ are independently of each other hydrogen or alkyl;

R$^5$ is hydrogen, alkyl, alkoxy, alkoxy-alkyl-, alkylthio, alkyl-NR$^{10}$—, alkenyl, alkenyloxy, alkynyl, benzyl, cycloalkyl-alkyl, phenyl-alkyl, R$^{10}$ is hydrogen or alkyl;

m is 0 when the dotted bond is present; and m is 1 when the dotted bond is absent; and A is a residue of formula a)

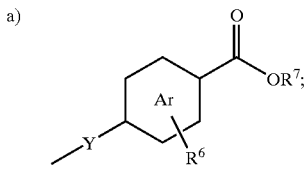

or of formula b)

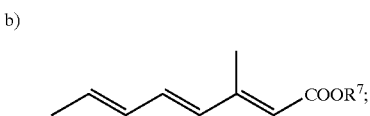

wherein

Ar is phenyl or a heteroarylic ring;

R$^6$ is hydrogen, halogen, alkoxy or hydroxy;

R$^7$ is hydrogen or alkyl; and

Y—COO—, —OCO—, —CON R$^{10}$—, —NR$^{10}$CO—, —CH═CH—, —C≡—C—, —COCH═CH—, —CHOHCH═CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—, with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, R$^5$ is hydrogen, alkyl, alkoxy-alkyl-, alkenyl, alkynyl, benzyl, cycloalkyl-alkyl or phenyl-alkyl;

and pharmaceutically active salts of carboxylic acids of formula I.

Activation of RAR has been associated with lung branching ald alveolization. The retinoids according to the invention possess RAR agonist activity. Therefore such compounds would be useful for the treatment of emphysema and related pulmonary diseases. They may also be useful for the therapy and prophylaxis of dermatological disorders which are accompanied by epithelial lesions, e.g. acne and psoriasis, light- and age-damaged skin; as well as for the promotion of wound healing, for example of incised wounds, such as surgical wounds, wounds caused by burns and other wounds caused by cutaneous trauma; and for the therapy and prophylaxis of malignant and premalignant epithelial lesions, tumours and precancerous changes of the mucous membrane in the mouth, tongue, larynx, oesophagus, bladder, cervix and colon.

DETAILED DESCRIPTION OF THE INVENTION

The term "alkyl" as used herein denotes straight chain or branched alkyl residues containing 1 to 10, preferably 1 to 7 carbon atoms, such as methyl, ethyl, isobutyl, pentyl, amyl and 3-pentyl, hexyl, heptyl, and the like; the alkyl chain may be substituted by amino, hydroxy, halogen. Such groups are for example hydroxymethyl, 2-hydroxyethyl, 3-hydroxypropyl, 4-hydroxybutyl, aminomethyl, 2-aminoethyl and the like.

As used herein, the term "alkoxy" refers to a straight or branched chain hydrocarbonoxy group wherein the "alkyl" portion is an alkyl group as defined above. Examples include methoxy, ethoxy, n-propoxy and the like.

As used herein, the term "alkoxy-alkyl-" refers to a dialkylether residue such as methoxymethyl, methoxyethyl, methoxypropyl, ethoxymethyl, ethoxyethyl, methoxyethoxymethyl and the like.

As used herein, the term "alkylthio" refers to a straight or branched chain hydrocarbonthio group wherein the "alkyl" portion is an alkyl group as defined above. Examples include methylthio, ethylthio, propylthio, and the like.

As used herein the term "alkenyl" refers to a straight or branched hydrocarbon chain radical having from 2 to 8 carbon atoms, preferably from 2 to 4 carbon atoms, and having at least one olefinic double bond, e.g. allyl, vinyl etc.

As used herein, the term "alkenyloxy" refers to a straight or branched chain hydrocarbonoxy group wherein the "alkenyl" portion is an alkenyl group as defined above. Examples include allyloxy, 3-butenyloxy and the like.

As used herein the term "alkynyl" refers to a straight or branched hydrocarbon chain radical having from 2 to 8 carbon atoms, preferably from 2 to 4 carbon atoms, and having at least one triple bond.

The term "cycloalkyl-alkyl" as used herein refers to alkyl groups as defined above bearing a cycloalkyl group having 3 to 7 carbon atoms as for example cyclopropylmethyl, cyclobutylmethyl, cyclopentylmethyl, cyclohexylmethyl, cyclopropylethyl, cyclobutylethyl, cyclopentylethyl, cyclohexylethyl and the like.

As used herein the term "phenyl-alkyl" refers to a alkyl group as defined above having a phenyl group attached to the terminal C-atom as benzyl, phenethyl, phenylpropyl and the like, the phenyl group may unsubstituted or substituted by alkyl or alkoxy.

The term "heteroarylic ring" as used herein refers to a 5 or 6-membered heteroaryl ring containing at least one hetero atom selected from oxygen, sulfur, and nitrogen for example to pyridinyl, furanyl or thiophenyl. In formulae I, I-1 and IA–IH, "Ar" surrounded by hexagon can indicate a heteroarylic ring having at least three ring carbon atoms, in which case the heteroarylic ring is bonded to each of Y, R$^6$ and —C(O)OR$^7$ via a different ring carbon atom. Alternatively Ar surrounded by hexagon can indicate phenyl, in which case Y and —C(O)OR$^7$ are para to each other.

The groups Y are shown in their orientation in the compound of formula I. By way of illustration when Y is —CONR$^{10}$—, the nitrogen is bonded directly to the group Ar.

The compounds of formula I, wherein R$^7$ is hydrogen, form salts with pharmaceutically acceptable bases such as alkali salts, e.g. Na- and K-salts, and ammonium or substituted ammonium salts such as trimethylammonium salts which are within the scope of this invention.

When n is 2 or 3 in the formulae given in this application, each occurrence of R$^8$ can be the same or different and each occurrence of R$^9$ can be the same or different. It is preferred that all occurrences of R$^8$ are the same as the others and that all occurrences of R$^9$ are the same as the others. When n is 1, 2 or 3, it is most preferred for each R$^8$ and each R$^9$ to be hydrogen.

Preferred compounds of formula I are the compounds of formula

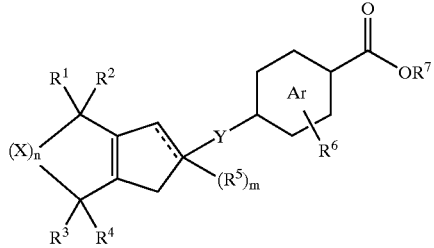

I-1 wherein
the dotted bond is present and forms a double bond, or is absent;
$R^1$, $R^2$, $R^3$, $R^4$ are independently of each other hydrogen or alkyl;
X is $R^8R^9C<$ for n=1, 2 or 3; or
X is oxygen for n=1;
$R^5$ is hydrogen, alkyl, alkoxy, alkenyl, alkenyloxy, alkynyl, benzyl, cycloalkyl-alkyl or phenylalkyl;
m is 0 when the dotted bond is present; or
m is 1 when the dotted bond is absent;
Ar is phenyl or heteroarylic ring;
$R^6$ is hydrogen, halogen, alkoxy or hydroxy;
$R^7$ is hydrogen or alkyl;
$R^8$ and $R^9$ are independently of each other hydrogen or alkyl; and Y—COO—, —OCO—, —CONH—, —NHCO—, —CH=CH—, —C≡C—, —COCH=CH—, —CHOHCH=CH—, —CH$_2$O—, —CH$_2$S— or —CH$_2$NH—; with the proviso that when Y is —OCO— or —NHCO—, $R^5$ is hydrogen, alkyl, alkenyl, alkynyl, benzyl, cycloalkyl-alkyl or phenylalkyl;
and pharmaceutically active salts of carboxylic acids of formula I-1.
Especially preferred are the compounds of formulas

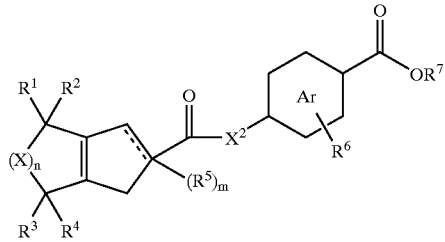

IA

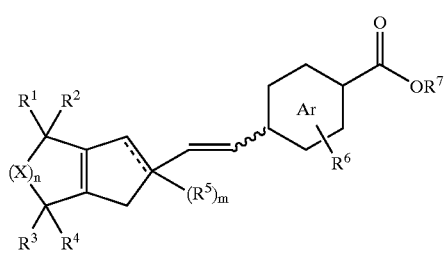

IB

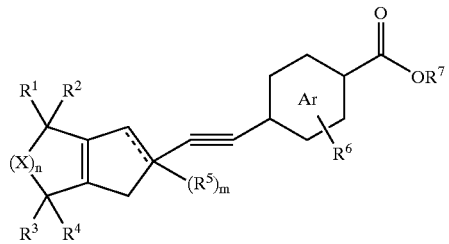

IC

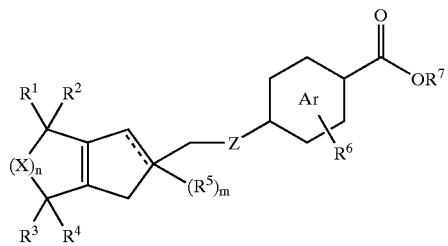

ID

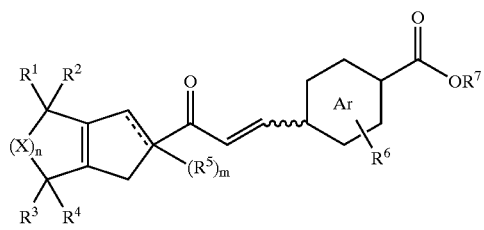

IE

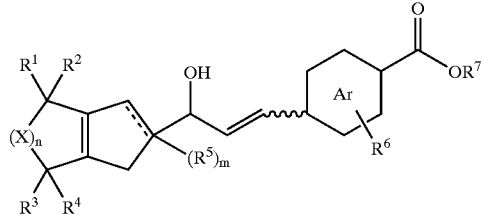

IF

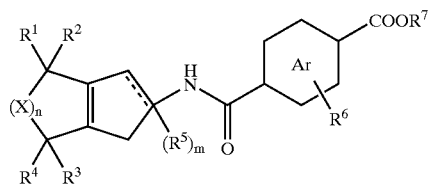

IG

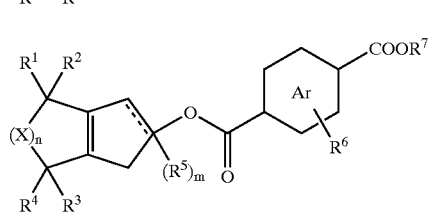

IH wherein the symbols are as defined above, $X^2$ is oxygen or —NH— and Z is oxygen, sulfur or —NH—;

and pharmaceutically active salts of carboxylic acids of formulae IA–IH.
The double bond in compounds of formulae IB, IE and IF may form an E/Z mixture or be E or Z configurated, preferably E configurated. The zigzag line in these formulae above indicates that the configuration can be E or Z.

Preferred compounds are those wherein X is R⁸R⁹C< and n is an integer 1 or 2.

Especially preferred are compounds of formula IA wherein $X^2$ is oxygen and n is 2, for example

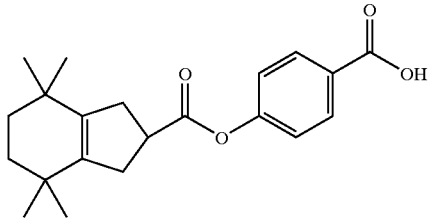

A 4,4,7,7-tetramethyl-2,3,4,5,6,7-hexahydro-1H-indene-2-carboxylic acid 4-carboxy-phenyl ester

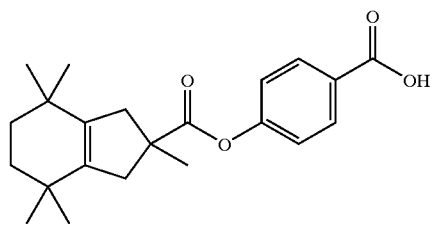

B 2,4,4,7,7-pentamethyl-2,3,4,5,6,7-hexahydro-1H-indene-2-carboxylic acid 4-carboxy-phenyl ester

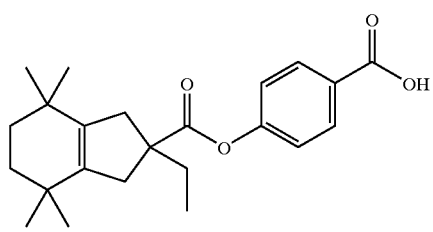

C 2-ethyl-4,4,7,7-tetramethyl-2,3,4,5,6,7-hexahydro-1H-indene-2-carboxylic acid 4-carboxy-phenyl ester

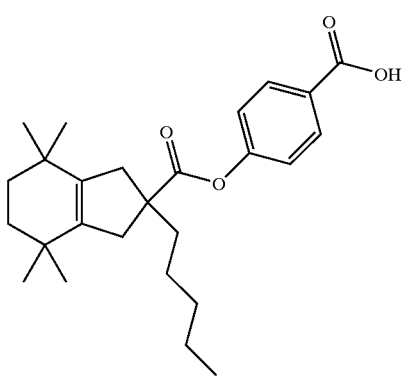

D 4,4,7,7-tetramethyl-2-pentyl-2,3,4,5,6,7-hexahydro-1H-indene-2-carboxylic acid 4-carboxy-phenyl ester

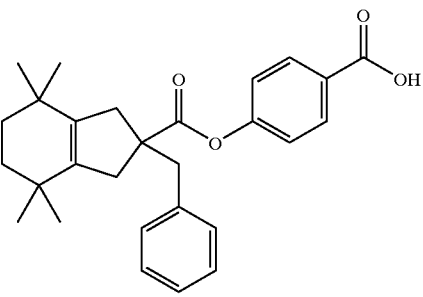

E 2-benzyl-4,4,7,7-tetramethyl-2,3,4,5,6,7-hexahydro-1H-indene-2-carboxylic acid 4-carboxy-phenyl ester 2-propyl-4,4,7,7-tetramethyl-2,3,4,5,6,7-hexahydro-1H-indene-2-carboxylic acid 4-carboxy-phenyl ester
2-butyl-4,4,7,7-tetramethyl-2,3,4,5,6,7-hexahydro-1H-indene-2-carboxylic acid 4-carboxy-phenyl ester
2-hexyl-4,4,7,7-tetramethyl-2,3,4,5,6,7-hexahydro-1H-indene-2-carboxylic acid 4-carboxy-phenyl ester
2-phenethyl-4,4,7,7-tetramethyl-2,3,4,5,6,7-hexahydro-1H-indene-2-carboxylic acid 4-carboxy-phenyl ester.

Further preferred are compounds of formula IA wherein Ar is pyridine, i.e.
6-[(4,4,7,7-tetramethyl-2-pentyl-2,3,4,5,6,7-hexahydro-1H-indene-2-carbonyl)-amino]-nicotinic acid

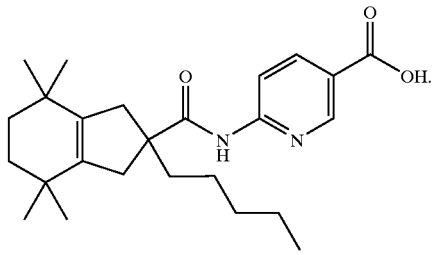

Further preferred are compounds of formula IA wherein n is 1 and X is R⁸R⁹C<:
4,4,6,6-tetramethyl-2-pentyl-1,2,3,4,5,6-hexahydro-pentalene-2-carboxylic acid 4-carboxy-phenyl ester;
and compounds wherein n is 1 and X is oxygen
1,1,3,3-tetramethyl-5-pentyl-3,4,5,6-tetrahydro-1H-cyclopenta[c]furan-5-carboxylic acid 4-carboxy-phenyl ester.

A further group of preferred compounds are compounds a) of formula IB:
4-[2-(4,4,7,7-tetramethyl-2-pentyl-2,3,4,5,6,7-hexahydro-1H-indene-2-yl)-vinyl]-benzoic acid;

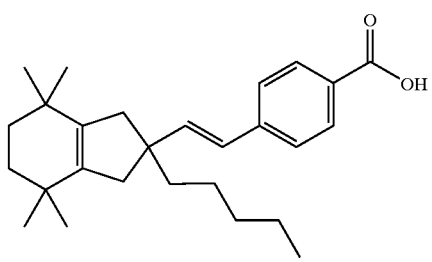

b) of formula IC:
4-(4,4,7,7-tetramethyl-2-pentyl-2,3,4,5,6,7-hexahydro-1H-indene-2-ylethynyl)-benzoic acid

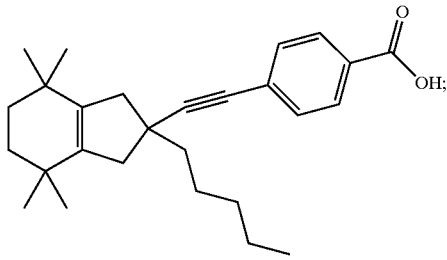

c) of formula ID, wherein Z is oxygen:
4-(4,4,7,7-tetramethyl-2-pentyl-2,3,4,5,6,7-hexahydro-1H-inden-2-ylmethoxy)-benzoic acid;
of formula ID, wherein Z is sulfur:
4-(4,4,7,7-tetramethyl-2-pentyl-2,3,4,5,6,7-hexahydro-1H-inden-2-ylmethylsulfanyl)-benzoic acid; and
of formula ID, wherein Z is —NH—:
4-[-(4,4,7,7-tetramethyl-2-pentyl-2,3,4,5,6,7-hexahydro-1H-inden-2-ylmethyl)-amino]-benzoic acid;
d) of formula IE
4-[3-oxo-3-(4,4,7,7-tetramethyl-2-pentyl-2,3,4,5,6,7-hexahydro-1H-indene-2-yl)-propenyl]benzoic acid; and
e) of formula IF
4-[3-hydroxy-3-(4,4,7,7-tetramethyl-2-pentyl-2,3,4,5,6,7-hexahydro-1H-inden-2-yl)-propenyl]-benzoic acid;

Further preferred compounds of formula I are the compounds of formula

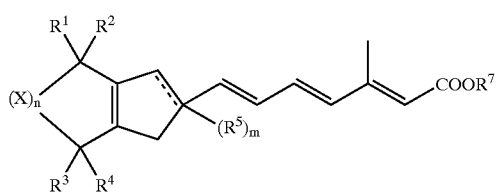

I-2 wherein
the dotted bond is present and forms a double bond, or is absent;

$R^1, R^2, R^3, R^4$ are independently of each other hydrogen or alkyl;
X is $R^8R^9C<$ for n=1, 2 or 3; or
X is oxygen for n=1;
$R^8$ and $R^9$ are independently of each other hydrogen or alkyl;
$R^5$ is hydrogen, alkyl, alkoxy, alkenyl, alkenyloxy, alkynyl, benzyl, cycloalkyl-alkyl, phenyl-alkyl;
m is 0 when the dotted bond is present; or
m is 1 when the dotted bond is absent; and
$R^7$ is hydrogen or alkyl;
and pharmaceutically active salts of carboxylic acids of formula I-2.

Especially preferred compounds of formula I-2 are
(2E,4E,6E)-3-methyl-7-(4,4,7,7-tetramethyl-2-pentyl-2,3,4,5,6,7-hexahydro-1H-inden-2-yl)-hepta-2,4,6-trienoic acid;

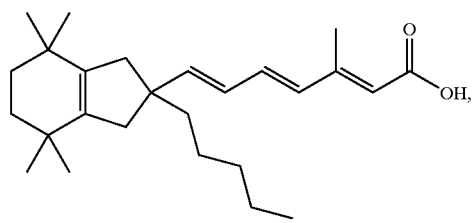

and (2Z,4E,6E)-3-methyl-7-(4,4,7,7-tetramethyl-2-pentyl-2,3,4,5,6,7-hexahydro-1H-inden-2-yl)-hepta-2,4,6-trienoic acid.

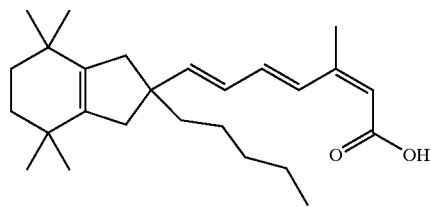

The compounds according to the invention can be prepared in a manner known in the art. In particular compounds of formula IA, wherein $X^2$ is oxygen or —NH— may for example be prepared according to scheme 1:

Scheme 1

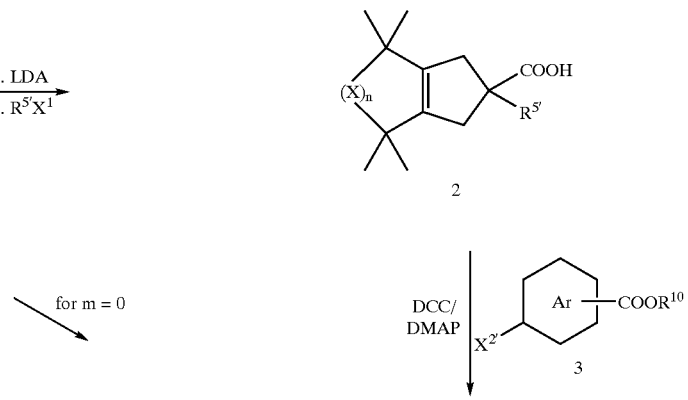

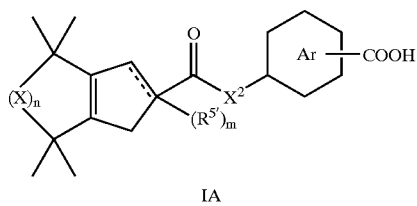

IA

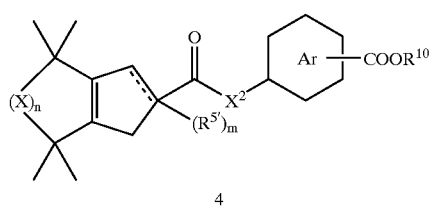

4 wherein X, n, m and Ar are defined as above and $R^{5'}$ is hydrogen, alkyl, alkoxy-alkyl-, alkenyl, alkynyl, benzyl, cycloalkyl-alkyl, phenyl-alkyl;

$X^1$ is a halogen, preferably bromide or iodide;

$X^{2'}$ is —OH or $NH_2$;

$X^2$ is oxygen or —NH—; and $R^{10}$ is $R^7$ or a carboxylic acid protecting group, preferably an allylic group.

LDA is lithium diisopropylamide; and

DCC/DMAP is dicyclohexylcarbodiimide/dimethylamino pyridine.

The acid 1, wherein the dotted line is absent and thus m is 1, can be alkylated with a suitable alkylhalogenide preferably an alkylbromide or an alkyliodide, or with an alkyl sulfonate, e.g. tosylate or mesylate, using a strong base, e.g. lithium diisopropylamide or potassium tert.-butylate, to give the alkylated acid 2, which is condensed with a hydroxy- or aminoaryl carboxylic acid ester 3 to give compound 4. In the alternative the alkylation step is omitted for compounds of formula IA, wherein the dotted bond is present and m is thus 0. As condensation agent dicyclohexylcarbodi-imide/4-dimethylaminopyridine can be used. Alternatively the acid 2 (or 1, respectively) can be transformed into the acid chloride (thionyl chloride, oxalyl chloride) and then reacted with compounds 3 and in the presence of a base (pyridine, triethylamine). $R^{10}$ in compound 3 can be $R^7$ when $X^{2'}$ is $NH_2$ or must be a carboxylic acid protecting group like allyl-, β-trimethylsilylethyl-, tert.-butyl- or 4-(trimethylsilyl)-2-buten-1-yl- or benzyl, when $X^{2'}$ is —OH. The carboxylic acid protecting group can be removed in the last step without cleavage of the internal amide or ester bond with such agents as Pd(0)/morpholine or Pd(0)/$Bu_3SnH$ for the allyl group, $Bu_4NF$ for the β-trimethylsilylethyl group, formic acid for the tert.-butyl group or Pd(0) for the 4-(trimethylsilyl)-2-buten-1-yl group or catalytic hydrogenation for the benzyl group.

The acid 1, wherein the dotted line is absent and thus m is 1, used as starting material can be prepared in analogy to the examples given in EP 116 277 and EP 115 274. The acid 1, wherein the dotted line is present and forms a double bond are prepared as depicted in scheme 1a below. Starting from the ester of formula 1a which is transformed to the corresponding unsaturated compound 1b as depicted in scheme 1a:

Scheme 1a:

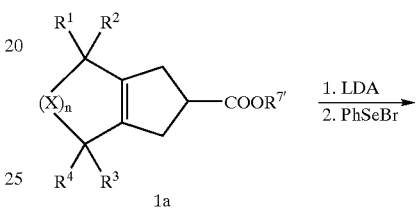

1a

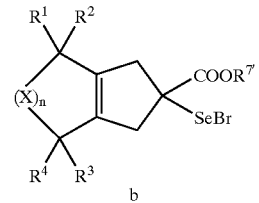

b

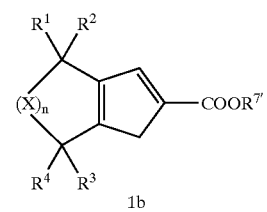

1b wherein the symbols are as defined above, $R^{7'}$ is alkyl, LDA is lithium diisopropylamide and Ph is phenyl.

Compounds of formula I, wherein Y is —CH=CH—, i.e. compounds of formula IB may be prepared according to scheme 2:

Scheme 2

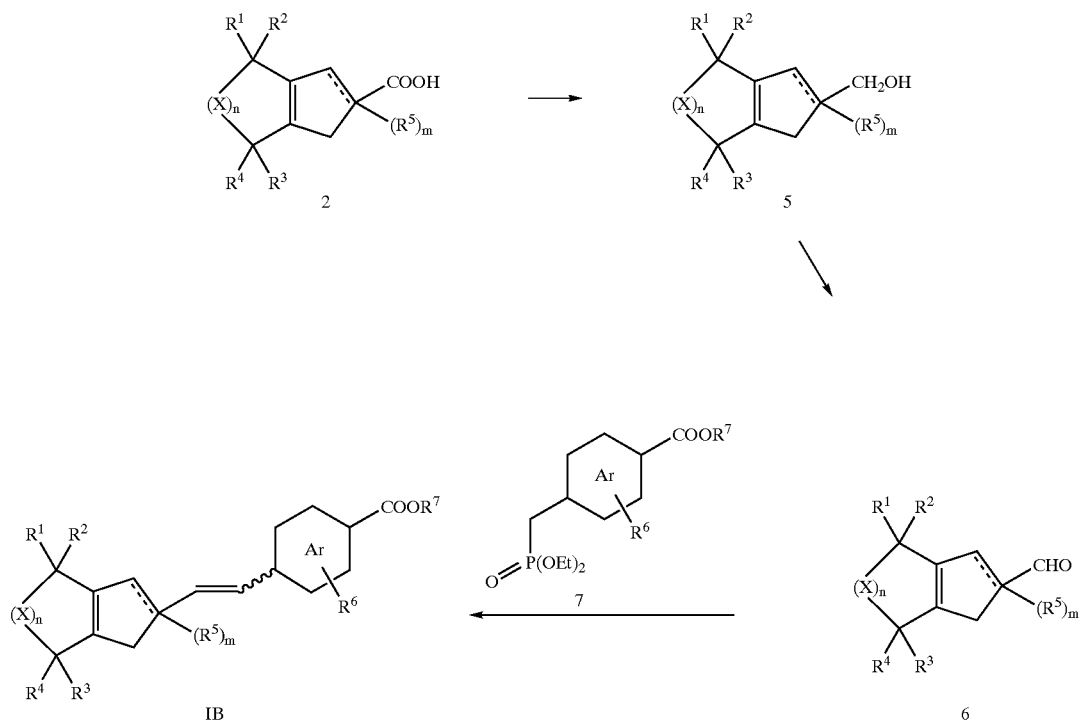

wherein the symbols are as defined above and Et signifies ethyl.

The acid 2 can be reduced to the alcohol 5 (e.g. with LiAlH₄, or a borane complex), oxidized to the aldehyde 6 by a Swern or a Dess-Martin oxidation or with pyridinium chlorochromate and then condensed in a Wittig-Horner reaction with a suitable phosphonate 7 using a strong base like NaH or lithium-bis-(trimethyl-silyl)-amide (LiHMDS) to give the olefinic compounds of formula IB wherein $R^7$ is different from hydrogen and which can be hydrolyzed if desired to a compound of formula IB wherein $R^7$ is hydrogen. The double bond may be in a E/Z mixture, or preferably in the E configuration. The Wittig-Horner reaction is highly trans selective and Scheme 2 illustrates the synthesis of the trans isomer. The corresponding cis isomer may be prepared in accordance with Scheme 3, followed by Lindlar reduction of the triple bond.

Compounds of formula I wherein Y is an acetylenic group (—C≡C—), namely compounds of formula IC can be prepared according to scheme 3:

Scheme 3:

wherein the symbols are as defined above and $X^3$ is halogen, preferably bromine or iodine.

The aldehyde 6 can be transformed into the acetylenic derivative 9 according to the method of Corey and Fuchs by reaction with $P(C_6H_5)_3/CBr_4$ and subsequently with butyllithium. The lithiated product is then coupled with a bromo or iodo substituted aromatic ester 8 in a Pd(0) catalyzed reaction to give a compound of formula IC wherein $R^7$ is different from hydrogen and which can be hydrolyzed to the product wherein $R^7$ is hydrogen if desired.

Compounds of formula I wherein Y is —$CH_2O$—, —$CH_2S$— or —$CH_2NR^{10}$—, i.e. compounds of formula ID, wherein Z is —O—, —S— or —NH—, can be synthesized according to Scheme 4 by using an alcohol 5 as starting material.

Scheme 4

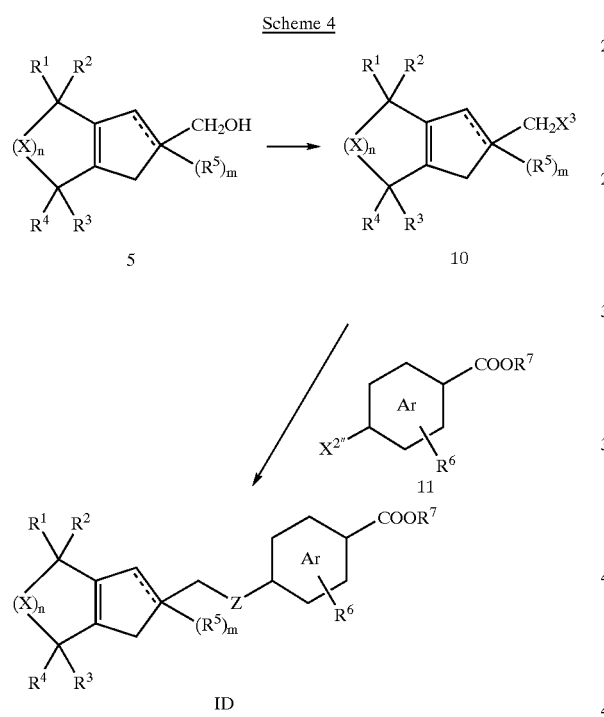

wherein the symbols are as defined above and $X^{2''}$ is —OH, —SH or —$NH_2$.

The hydroxy group of the alcohol 5 can be transformed to the halogenated derivative 10 with $PX_3^3$ or $CX_4^3/(C_6H_5)_3P$, wherein $X^3$ is a halogenide preferably a chloride or bromide, or to a sulfonate using mesyl chloride or tosyl chloride followed by reaction with compound 11 to give the product of formula ID, which may be hydrolyzed to the product of formula ID wherein $R^7$ is hydrogen.

Compounds of formula ID, wherein Z is sulfur can be oxidized to the sulfoxide or the sulfone with peroxides. An alternative method for the synthesis of compounds of formula ID wherein Z is oxygen or sulfur is according to Mitsunobu by reacting the alcohol 5 with compound 11 wherein $X^{2''}$ is OH or SH.

Compounds of formula I, wherein Y is —COCH=CH—, i.e. compounds of formula IE can be synthesized according to scheme 5.

Scheme 5

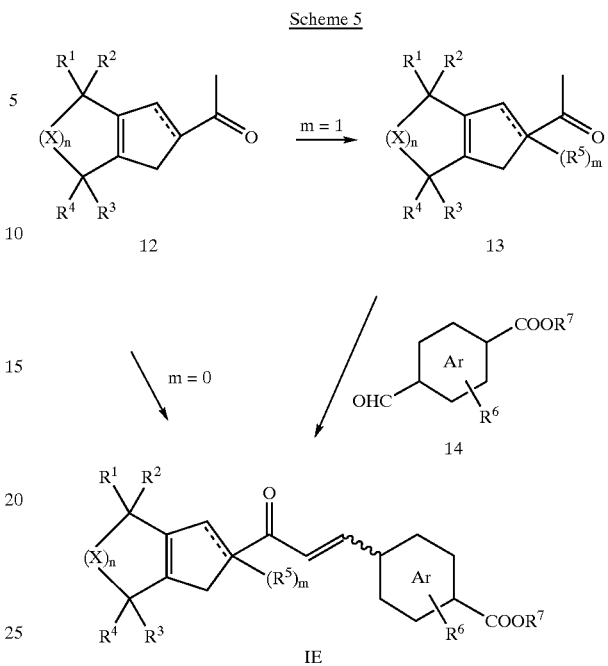

wherein the symbols are as defined above.

The ketone 12 can be alkylated at the higher substituted position by using sodium hydride (NaH), potassium hydride (KH) or potassium tert.-butylate as a base to give compounds 13 wherein the dotted bond is absent and m is 1. Aldol condensation of compounds 12 or 13, respectively, with formyl compound 14 in the presence of catalytic amounts of sodium hydroxyde (NaOH), piperidine, piperidinium acetate or piperidinium tosylate yields compounds of formula IE wherein $R^7$ is different from hydrogen which can be transformed into the final product IE wherein $R^7$ is hydrogen by hydrolysis of the ester group.

Compound of formula I, wherein Y is —CHOHCH=CH—, i.e. compounds of formula IF can be prepared according to scheme 6 by reduction of a compound of formula IE with for example $NaBH_4$ or with $NaBH_4/CeCl_3$.

Scheme 6

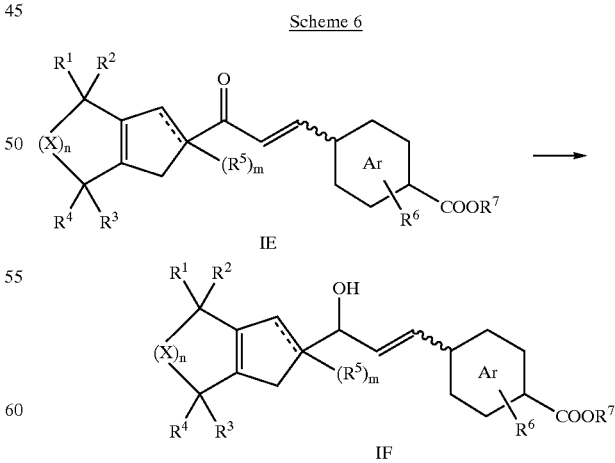

wherein the symbols are as defined above.

Compounds of formula IF wherein $R^7$ is different from hydrogen can be transformed into the product IF wherein $R^7$ is hydrogen by hydrolysis.

The compounds of formula I, wherein Y is —NR$^{10}$CO—, i.e. compounds of formula IG can be prepared according to scheme 7. Various methods are known for the transformation of acid 2 into amine 15 (Hofmann, Lossen, Curtius or Schmidt-rearrangement)

Scheme 7

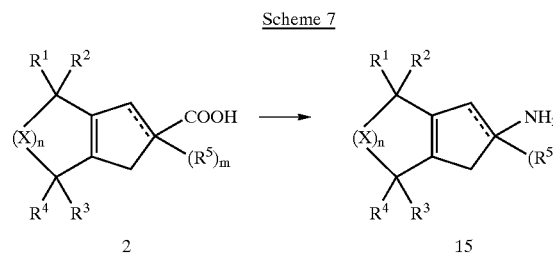

2

15

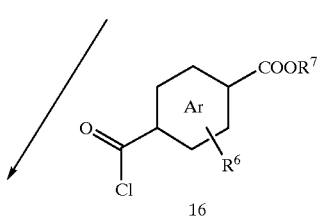

16

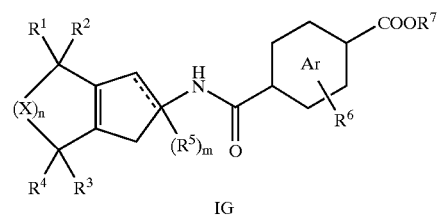

IG wherein the symbols are as defined above.

The amine 15 for example can be reacted with a terephthalic acid chloride derivative or a suitable acid chloride 16 in presence of pyridine or triethyl amine to give the amide of formula IG wherein R$^7$ is different from hydrogen. Hydrolysis of the ester group yields the product of formula IG wherein R$^7$ is hydrogen.

In the alternative the internal amide bond can also be formed by reaction of the amine 15 with terephthalic acid half ester and dicyclohexylcarbodiimide.

Compounds of formula I, wherein Y is —OCO—, i.e. compounds of formula IH can be synthesized according to scheme 8.

Compound 12 can be oxidized according to Baeyer-Villiger with a peroxyacid to give the hydroxy compound 17. Esterification is performed using known methods as for example by reaction of an acid chloride 16 and a base.

Scheme 8

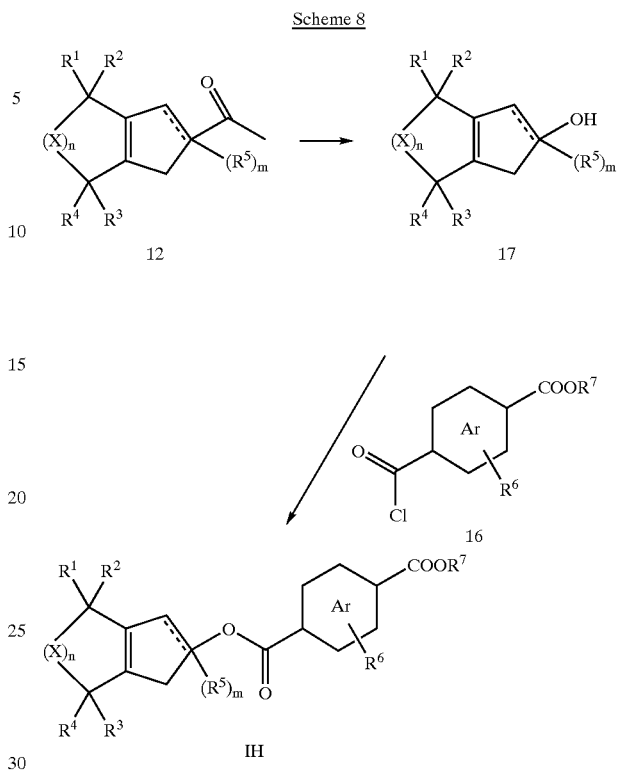

wherein the symbols are as defined above.

Compounds of formula I-2 can be prepared according to the method depicted in Scheme 9:

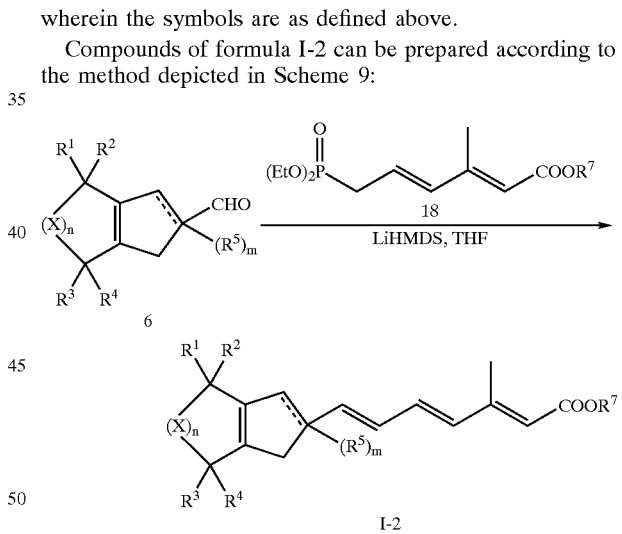

wherein the symbols are as defined above.

The aldehyde 6 is reacted with the phosphonate 18 in a Wittig-Horner reaction in presence of a strong base as for example sodium hydride or lithium-bis-(trimethylsilyl)-amide (LiHMDS) in an inert solvent as for example THF to the ester of formula I-2, wherein R$^7$ is alkyl. This ester may subsequently be hydrolyzed to the compound of formula I-2, wherein R$^7$ is hydrogen.

Compounds of formula I, wherein R$^5$ is alkoxy, alkylthio and alkyl-NR$^{10}$— and Y is different from —OCO—, —NHCO—, —OCH$_2$—, —SCH$_2$—, —SOCH$_2$—, —SO$_2$CH$_2$— or —NR$^{10}$CH$_2$— can be prepared by known methods for example they may be prepared according to the methods depicted in scheme 10.

Scheme 10

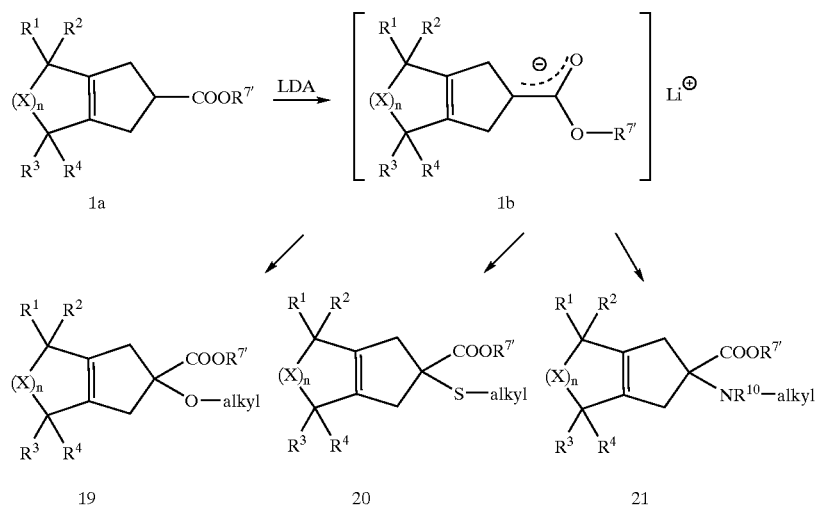

wherein the symbols are as defined above.

The ester 1a can be transformed into the ester enolate 1b in presence of a strong, non-nucleophilic base like lithium diisopropylamide, this enolate can then be reacted with:

a) MoO$_5$-complex to give the corresponding α-hydroxy compound which can then be alkylated with an alkyl-halogenide (R$^5$X$^1$) to form compound 19 which is then transformed according to one of the reaction schemes above into the desired compound of formula I;

b) a suitable disulfide alkyl-S—S-alkyl to give the corresponding α-thioester 20;

c) a [NH$_2$$^⊕$]-synthon (for a review of such synthons see G. Boche in Houben-Weyl, Methods of Organic Chemistry, Vol. E21e, p.5133 (1995) or D. Enders et al. in Tetrahedron 1998, 54, 10069).

Compounds of formula IA, wherein Y is —OCH$_2$—, —SCH$_2$—, —SOCH$_2$—, —SO$_2$CH$_2$— or —NR$^{10}$CH$_2$— and R$^5$ is alkyl, alkoxy-alkyl-, alkenyl, alkynyl, benzyl, cycloalkyl-alkyl, phenyl-alkyl, can be prepared according to the method depicted in scheme 11:

Scheme 11:

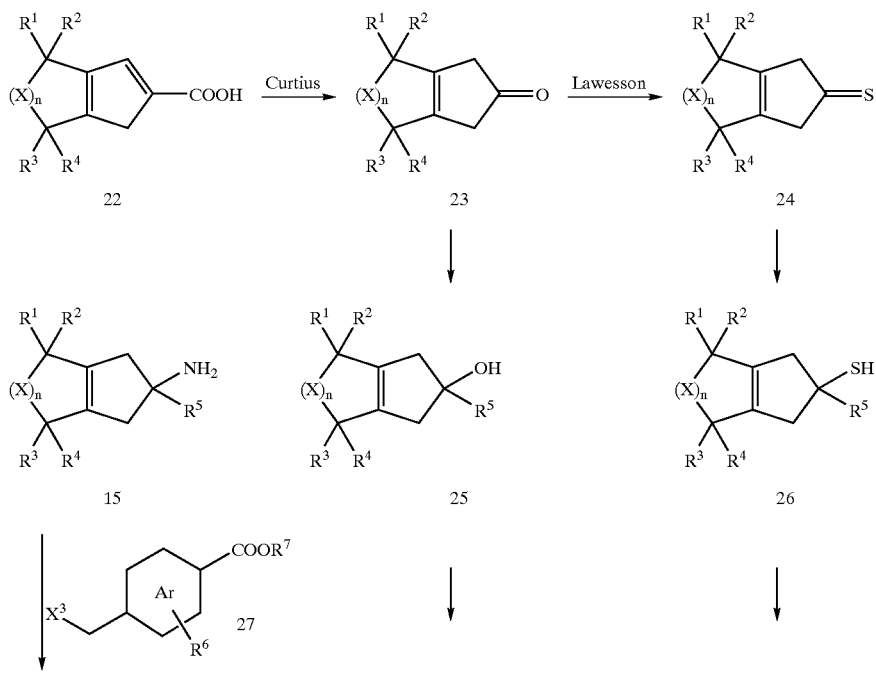

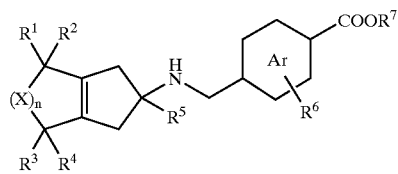 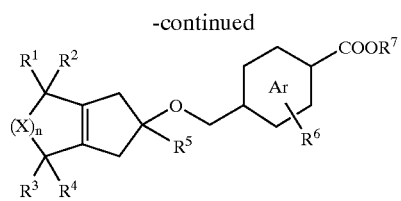 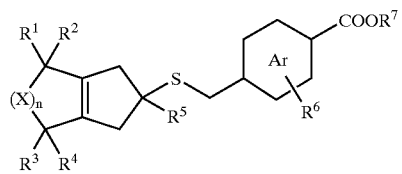

I, wherein
Y is —NHCH$_2$—

I, wherein
Y is —OCH$_2$—

I, wherein
Y is —SCH$_2$— wherein the symbols are as defined above.

The acid 22, synthesis described in example 11, can be transformed in a Curtius reaction into the corresponding ketone 23 which will react with Lawesson reagent to the thioketone 24. Addition of a Grignard reagent will lead to compounds 25 and 26, respectively. Alkylation of compounds 15, 25 or 26 with bromomethyl derivative 27 will give the desired products of formula IA, wherein Y is —NHCH—, —OCH$_2$— or —SCH$_2$—.

In another aspect, this invention is concerned with the use of RAR selective agonist with systemic administration being a preferred mode of delivery for treating emphysema and associated pulmonary diseases. It is thus concerned with a method for treating emphysema and associated pulmonary diseases by treatment of a mammal with a RAR selective agonist with systemic administration being a preferred mode of delivery.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the mammal to be treated.

The RARγ agonist selectivity of a compound can be determined by routine ligand binding assays known to one of skill in the art such as described in C. Apfel et al. *Proc. Nat. Sci. Acad.* (*USA*), 89:7129–7133 (1992); M. Teng et al., *J. Med. Chem.*, 40:2445–2451 (1997); and PCT Publication WO 96/30009.

The uses of RAR agonists disclosed herein may be used for promoting the repair of damaged alveoli and septation of new alveoli, particularly for the treatment emphysema. Treatment with RAR agonists, particularly, RARγ selective agonists is useful to promote repair of alveolar matrix and septation. As such, the methods disclosed herein are useful for treating diseases such as emphysema.

Typically, the dosage will range between about 0.01 and 1.0 mg/kg body weight per day, preferably from about 0.05 to about 0.5 mg/kg body weight per day.

In particular dosage of a RAR selective agonist required to treat lung emphysema will depend on the severity of the condition. This dosage may be delivered in a conventional pharmaceutical composition by a single administration, by multiple applications, or via controlled release, as needed to achieve the most effective results. Dosing will continue for as long as is medically indicated, which depending on the severity of the disease may range from a few weeks to several months.

Typically, a pharmaceutically acceptable composition, such as a salt, of the RAR agonist of formula I in a pharmaceutically acceptable carrier or diluent is administered. In the context of the present invention, pharmaceutically acceptable salts include any chemically suitable salt known in the art of retinoid agonists as applicable for administration to human patients. Examples of conventional salts known in the art include the alkali metal salts such as sodium and potassium salts, the alkaline earth metal salts such as calcium and magnesium salts, and ammonium and alkyl ammonium salts.

Representative delivery regimens include oral, parenteral (including subcutaneous, intramuscular and intravenous), rectal, buccal (including sublingual), transdermal, pulmonary and intranasal. One method of pulmonary administration involves aerosolization of an aqueous solution of an RAR agonist. Aerosolized compositions may include the compound packaged in reverse micelles or liposomes. Typical pulmonary and respiratory delivery systems are described in U.S. Pat. Nos. 5,607,915, 5,238,683, 5,292,499, and 5,364,615.

The treatment methods of this invention also include systemic administration of RAR agonists in simultaneous or sequential combination with a further active ingredient.

RAR agonists will typically be administered as pharmaceutical compositions in admixture with a pharmaceutically acceptable, non toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. The carrier material can be any organic or inorganic carrier material, such as water, gelatin, gum arabic, lactose, starch, magnesium stearate, talc, polyalkylene glycols, petroleum jelly and the like.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcarnitines.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Solid forms for oral administration include tablets, hard and soft gelatin capsules, pills, sachets, powders, granules and the like. Each tablet, pill or sachet may contain from about 1 to about 50 mg, preferably from 5 to about 10 mg of RAR agonist. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; Pharmaceutical Technology, 9, (1985). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because the dry shell.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR selective agonists as described herein for promoting elastin mediated matrix repair and alveolar septation.

Tablet Formulation

The following ingredients are mixed intimately and pressed into single scored tablets.

| Quantity per Ingredient | tablet, mg |
|---|---|
| RAR agonist | 10 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| RAR agonist | 5 |
| lactose, spray-dried | 148 |
| magnesium stearate | 2 |

Suspension Formulation

The following ingredients are mixed to form a suspension for oral administration.

| Ingredient | Amount |
|---|---|
| RAR agonist | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| RAR agonist | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

Nasal Formulation

The following ingredients are mixed to form a suspension for nasal administration.

| Ingredient | Amount |
|---|---|
| RAR agonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following preparations and examples are given to enable those skilled in the art to more clearly understand and to practice the present invention. They should not be considered as limiting the scope of the invention, but merely as being illustrative and representative thereof.

EXAMPLE 1

Preparation of 4,4,7,7-tetramethyl-2-pentyl-2,3,4,5,6,7-hexahydro-1H-indene-2-carboxylic acid 13.6 g of diisopropylamine were dissolved in 200 ml of THF (tetrahydrofuran) abs. and treated dropwise at −10° with 84 ml of butyl lithium (1.6 molar in hexane). After 15 minutes of stirring at 0° C., a solution of 12 g of 4,4,7,7-tetramethyl-2,3,4,5,6,7-hexahydro-1H-indene-2-carboxylic acid in 40 ml of THF was dropped in. The reaction mixture was stirred for one hour at room temperature, cooled again to 0° C. and treated dropwise with a solution of 26.4 g of pentyl iodide in 30 ml of THF. After stirring for 90 minutes at room temperature, the reaction mixture was poured onto ice/water, acidified with 3N HCl and extracted with ethyl acetate. The organic phase was washed with water, dried over $Na_2SO_4$ and evaporated to yield a pale yellow, partially crystalline oil. Flash chromatography ($SiO_2$, hexane/ethyl acetate=6:1) and crystallization from pentane yielded 12.9 g of 4,4,7,7-tetramethyl-2-pentyl-2,3,4,5,6,7-hexahydro-1H-indene-2-carboxylic acid as white crystals, m.p. 57–58° C.

In analogy to Example 1.1. by using a corresponding alkyl iodide the following compound were synthesized:

2,4,4,7,7-Pentamethyl-2,3,4,5,6,7-hexahydro-1H-indene-2-carboxylic acid, m.p. 132–134° C.

2-Ethyl-4,4,7,7-tetramethyl-2,3,4,5,6,7-hexahydro-1H-indene-2-carboxylic acid, m.p. 108–109° C.

2-Benzyl-4,4,7,7-tetramethyl-2,3,4,5,6,7-hexahydro-1H-indene-2-carboxylic acid, m.p. 118–120° C.

2-Propyl-4,4,7,7-tetramethyl-2,3,4,5,6,7-hexahydro-1H-indene-2-carboxylic acid, m.p. 110–112° C.

2-Butyl-4,4,7,7-tetramethyl-2,3,4,5,6,7-hexahydro-1H-indene-2-carboxylic acid, m.p. 89–90° C.

2-Isobutyl-4,4,7,7-tetramethyl-2,3,4,5,6,7-hexahydro-1H-indene-2-carboxylic acid, m.p. 87–88° C.

2-Hexyl-4,4,7,7-tetramethyl-2,3,4,5,6,7-hexahydro-1H-indene-2-carboxylic acid, m.p. 68–69° C.

2-Phenethyl-4,4,7,7-tetramethyl-2,3,4,5,6,7-hexahydro-1H-indene-2-carboxylic acid, m.p. 121–122° C.

EXAMPLE 2

2.1. Preparation of 4,4,7,7-tetramethyl-2-pentyl-2,3,4,5,6,7-hexahydro-1H-indene-2-carboxylic acid 4-allyoxycarbonyl-phenyl ester 14.5 g of 4,4,7,7-Tetramethyl-2-pentyl-2,3,4,5,6,7-hexahydro-1H-indene-2-carboxylic acid were dissolved in 200 ml of methylene chloride. A solution of 9.7 g of 4-hydroxybenzoic acid alkyl ester in 160 ml of methylene chloride was added, followed by 6 g of 4-dimethylaminopyridine. The reaction mixture was cooled to 0° C., treated with 11.3 g of 1,3-dicyclohexylcarbodiimide and stirred for 2 hours at 0° C. and 2 hours at room temperature. The reaction mixture was filtered, the precipitate washed with methylene chloride, the organic phase washed with water, dried over $Na_2SO_4$ and evaporated. The partially crystalline residue was stirred with 200 ml of hexane for 1 hour at room temperature, filtered again and the filtrate evaporated. The oily product was purified by column chromatography ($SiO_2$, hexane/ethyl acetate 2%) and afforded pure 4,4,7,7-tetramethyl-2-pentyl-2,3,4,5,6,7-hexahydro-1H-indene-2-carboxylic acid 4-alkyloxycarbonyl-phenyl ester as colorless oil.

In analogy to Example 2.1. by using the accordingly alkylated acids of Example 1, the following compounds were synthesized:

2.2. 2,4,4,7,7-Pentamethyl-2,3,4,5,6,7-hexahydro-1H-indene-2-carboxylic acid 4-allyloxycarbonyl-phenyl ester, m.p. 82–84° C.

2.3. 2-Ethyl-4,4,7,7-tetramethyl-2,3,4,5,6,7-hexahydro-1H-indene-2-carboxylic acid 4 allyloxycarbonyl-phenyl ester, m.p. 44–46° C.

2.4. 2-Benzyl-4,4,7,7-tetramethyl-2,3,4,5,6,7-hexahydro-1H-indene-2-carboxylic acid 4-allyloxycarbonyl-phenyl ester, m.p. 45–47° C.

2.5. 2-Propyl-4,4,7,7-tetramethyl-2,3,4,5,6,7-hexahydro-1H-indene-2-carboxylic acid 4-allyloxycarbonyl-phenyl ester as a colorless oil.

2.6. 2-Butyl-4,4,7,7-tetramethyl-2,3,4,5,6,7-hexahydro-1H-indene-2-carboxylic acid 4-allyloxycarbonyl-phenyl ester as a colorless oil.

2.7. 2-Isobutyl-4,4,7,7-tetramethyl-2,3,4,5,6,7-hexahydro-1H-indene-2-carboxylic acid 4-allyloxycarbonyl-phenyl ester as a colorless oil.

2.8. 2-Hexyl-4,4,7,7-tetramethyl-2,3,4,5,6,7-hexahydro-1H-indene-2-carboxylic acid 4-allyloxycarbonyl-phenyl ester as a colorless oil.

2.9. 2-Phenethyl-4,4,7,7-tetramethyl-2,3,4,5,6,7-hexahydro-1H-indene-2-carboxylic acid 4-allyloxycarbonyl-phenyl ester as a colorless oil.

EXAMPLE 3

3.1. Preparation of 4,4,7,7-tetramethyl-2-pentyl-2,3,4,5,6,7-hexahydro-1H-indene-2-carboxylic acid 4-carboxy-phenyl ester 19.2 g of 4,4,7,7-tetramethyl-2-pentyl-2,3,4,5,6,7-hexahydro-1H-indene-2-carboxylic acid 4-allyloxycarbonyl-phenyl ester were dissolved in 460 ml of THF. The reaction flask was evacuated and ventilated with argon twice. 4.6 g of tetrakis (triphenylphosphine) palladium were added, followed by 37 g of morpholine. The reaction mixture was stirred for 4 hours at room temperature, poured on 1500 ml of ice/water, acidified with 6N HCl and extracted with ethyl acetate. The organic phase was washed with water, dried over $Na_2SO_4$ and evaporated to yield a yellow solid. Purification by column chromatography ($SiO_2$, hexane/ethyl acetate=1:3) and crystallization from ethyl acetate/hexane afforded 12.9 g of 4,4,7,7-tetramethyl-2-pentyl-2,3,4,5,6,7-hexahydro-1H-indene-2-carboxylic acid 4-carboxy-phenyl ester, m.p. 156–158° C.

In analogy to Example 3.1. by using the alkyl esters of Example 2, the following compounds were synthesized:

3.2. 2,4,4,7,7-Pentamethyl-2,3,4,5,6,7-hexahydro-1H-indene-2-carboxylic acid 4-carboxy-phenyl ester, m.p. 205–206° C.

3.3. 2-Ethyl-4,4,7,7-tetramethyl-2,3,4,5,6,7-hexahydro-1H-indene-2-carboxylic acid 4-carboxy-phenyl ester, m.p. 175–176° C.

3.4. 2-Benzyl-4,4,7,7-tetramethyl-2,3,4,5,6,7-hexahydro-1H-indene-2-carboxylic acid 4-carboxy-phenyl ester, m.p. 183–184° C.

3.5. 4,4,7,7-Tetramethyl-2-propyl-2,3,4,5,6,7-hexahydro-1H-indene-2-carboxylic acid 4-carboxy-phenyl ester, m.p. 156–157° C.

3.6. 2-Butyl-4,4,7,7-tetramethyl-2,3,4,5,6,7-hexahydro-1H-indene-2-carboxylic acid 4-carboxy-phenyl ester, m.p. 172–173° C.

3.7. 2-Isobutyl-4,4,7,7-tetramethyl-2,3,4,5,6,7-hexahydro-1H-indene-2-carboxylic acid 4-carboxy-phenyl ester, m.p. 194–196° C.

3.8. 2-Hexyl-4,4,7,7-tetramethyl-2,3,4,5,6,7-hexahydro-1H-indene-2-carboxylic acid 4-carboxy-phenyl ester, m.p. 149–150° C.

3.9. 4,4,7,7-Tetramethyl-2-phenethyl-2,3,4,5,6,7-hexahydro-1H-indene-2-carboxylic acid 4-carboxy-phenyl ester, m.p. 182–183° C.

EXAMPLE 4

4.1. Preparation of 4,4,7,7-tetramethyl-2,3,4,5,6,7-hexahydro-1H-indene-2-carboxylic acid 4-allyloxycarbonyl-phenyl ester In analogy to Example 2.1 by using 4,4,7,7-tetramethyl-2,3,4,5,6,7-hexahydro-1H-indene-2-carboxylic acid as starting material, 4,4,7,7-tetramethyl-2,3,4,5,6,7-hexahydro-1H-indene-2-carboxylic acid 4-alkyloxycarbonyl-phenyl ester with a melting point of 48–50° C. was synthesized.

EXAMPLE 5

5.1. Preparation of 4,4,7,7-tetramethyl-2,3,4,5,6,7-hexahydro-1H-indene-2-carboxylic acid 4-carboxy-phenyl ester In analogy to Example 3 by using the alkyl ester of Example 4.1. as starting material 4,4,7,7-tetramethyl-2,3,4,5,6,7-hexahydro-1H-indene-2-carboxylic acid 4-carboxy-phenyl ester with a melting point of 194–195° C. was synthesized.

EXAMPLE 6

Preparation of 6-[(4,4,7,7-tetramethyl-2-pentyl-2,3,4,5,6,7-hexahydro-1H-indene-2-carbonyl)-amino]-nicotinic acid

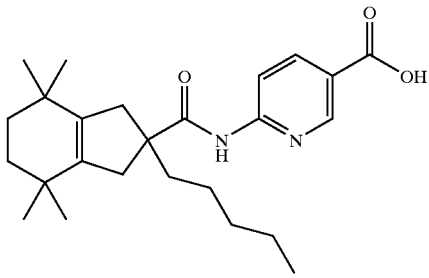

1 g of 4,4,7,7-tetramethyl-2-pentyl-2,3,4,5,6,7-hexahydro-1H-indene-2-carboxylic acid was dissolved in 20 ml of methylene chloride and treated at 0° C. with 1 ml of oxalyl chloride and two drops of DMF (dimethylformamide). After 4 hours of stirring at room temperature, the solution was evaporated, the oily residue dried for 1 hour in high vacuum, dissolved in 25 ml of pyridine and treated with 570 mg of 6-amino-nicotinic acid ethyl ester. After stirring at room temperature over night, the reaction mixture was poured on ice/water, acidified with 2 N HCL and extracted with ethyl acetate. The organic phase was dried (Na$_2$SO$_4$), the solvent evaporated and the residue purified with flash chromatography (silica gel, hexane/ethyl acetate=6:1) to yield 0.9 g of crystalline 6-[(4,4,7,7-tetramethyl-2-pentyl-2,3,4,5,6,7-hexahydro-1H-indene-2-carbonyl)-amino]-nicotinic acid ethyl ester, m.p. 92–93° C., after recrystallisation from pentane.

The ester was dissolved in 20 ml of ethanol and treated with a solution of 1 g of KOH (potassium hydroxyde) in 2 ml of water. After 2 hours at 40° C. the reaction mixture was poured on ice/water, acidified with 2 N HCl and extracted with ethyl acetate. The organic phase was dried (Na$_2$SO$_4$) and the solvent evaporated. The residue was crystallized from ethyl acetate/pentane and gave 0.6 g of 6-[(4,4,7,7-tetramethyl-2-pentyl-2,3,4,5,6,7-hexahydro-1H-indene-2-carbonyl)-amino]-nicotinic acid as colorless crystals, m.p. 172–174° C.

EXAMPLE 7

Preparation of 4-[2-(4,4,7,7-tetramethyl-2-pentyl-2,3,4,5,6,7-hexahydro-1H-inden-2-yl)vinyl]-benzoic acid

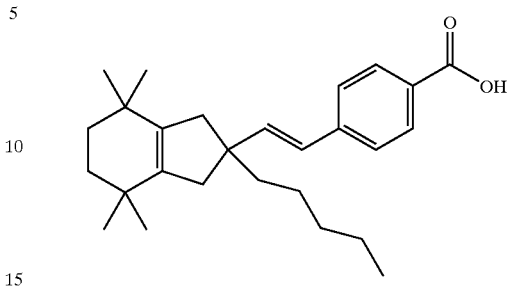

3.5 g of 4,4,7,7-tetramethyl-2-pentyl-2,3,4,5,6,7-hexahydro-1H-indene-2-carboxylic acid were dissolved in 35 ml of THF and treated dropwise at room temperature with a solution of 1.4 ml of borane methylsulfide in 10 ml of THF. The reaction mixture was stirred for 2 hours, then treated dropwise with 13 ml of methanol and evaporated. The yellow, oily residue was purified with flash chromatography (silica gel, hexane/ethyl acetate=5:1) to yield 2.9 g of (4,4,7,7-tetramethyl-2-pentyl-2,3,4,5,6,7-hexahydro-1H-inden-2-yl)-methanol as colorless oil.

2 ml of oxalyl chloride were dissolved in 100 ml of methylene chloride and treated at −70° C. dropwise with 2.8 g of dimethylsulfoxide. The reaction mixture was warmed for 5 minutes to −35° C., cooled again to −60° C. and treated dropwise with a solution of 2.9 g of (4,4,7,7-tetramethyl-2-pentyl-2,3,4,5,6,7-hexahydro-1H-inden-2-yl)-methanol in 20 ml of methylene chloride. After 15 minutes of stirring at −50° C., 5 ml of triethylamine were added dropwise. The reaction mixture was stirred at room temperature for 3 hours, then poured onto ice/water, extracted with methylene chloride, dried (Na$_2$SO$_4$) and the solvent was evaporated. The yellow, oily residue was purified with flash chromatography (silica gel, hexane/ethyl acetate=20:1) to yield 2.8 g of 4,4,7,7-tetramethyl-2-pentyl-2,3,4,5,6,7-hexahydro-1H-indene-2-carbaldehyde as colorless oil.

0.7 g of 4-(diethoxy-phosphorylmethyl)-benzoic acid ethyl ester were dissolved in 10 ml of THF and treated at −20° C. with 2.2 ml of a 1 molar solution of lithium bis(trimethylsilyl)amide in hexane. After 15 minutes a solution of 0.46 g of 4,4,7,7-tetramethyl-2-pentyl-2,3,4,5,6,7-hexahydro-1H-indene-2-carbaldehyde in 5 ml of THF was added. The reaction mixture was stirred for 3 hours at room temperature, poured on ice cold, saturated aqueous ammonium chloride solution, extracted with ethyl acetate, the organic phase was dried (Na$_2$SO$_4$) and the solvent evaporated. The yellow, oily residue was purified with flash chromatography (silica gel, hexane/10% ethyl acetate) and gave 0.73 g of (E)-4-[2-(4,4,7,7-tetramethyl-2-pentyl-2,3,4,5,6,7-hexahydro-1H-inden-2-yl)-vinyl]-benzoic acid ethyl ester as colorless oil.

The ester (0.7 g) was dissolved in 10 ml of ethanol and treated with a solution of 1.8 g of KOH in 5 ml of water. After having added 4 ml of THF, the reaction mixture was reacted for 3 hours at 40° C., poured on ice/water, acidified with 2N HCL and extracted with ethyl acetate. The organic phase was dried (Na$_2$SO$_4$), the solvent evaporated, and the crystalline residue recrystallized from pentane to give 0.4 g of 4-[2-(4,4,7,7-tetramethyl-2-pentyl-2,3,4,5,6,7-hexahydro-1H-inden-2-yl)-vinyl]-benzoic acid as colorless crystals, m.p. 121–123° C.

EXAMPLE 8

Preparation of 4-(4,4,7,7-tetramethyl-2-pentyl-2,3,4,5,6,7-hexahydro-1H-inden-2-yl-ethynyl)benzoic acid

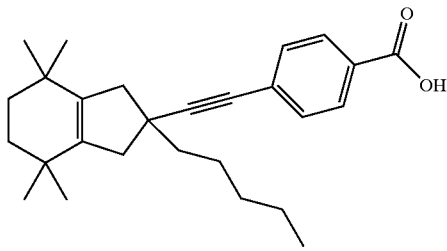

4.9 g of carbon tetrabromide were dissolved in 75 ml of methylene chloride and treated dropwise with a solution of 7.7 g of triphenylphosphine in 80 ml of methylene chloride at a temperature of −20° C. The slightly orange solution was stirred at 0° C. for 15 minutes, then treated with a solution of 2 g of 4,4,7,7-tetramethyl-2-pentyl-2,3,4,5,6,7-hexahydro-1H-indene-2-carbaldehyde in 20 ml of methylene chloride. the reaction mixture was stirred at room temperature for 2 hours, then poured on ice/water and diluted aqueous sodium bicarbonate solution and extracted with methylene chloride. The yellow oil which was received after drying of the organic phase and evaporation of the solvent, was further purified with flash chromatography (silica gel, hexane/ethyl acetate=20:1) to give 2-(2,2-dibromo-vinyl)-4,4,7,7-tetramethyl-2-pentyl-2,3,4,5,6,7-hexahydro-1H-indene as a slightly yellow oil.

0.6 g of this dibromide were dissolved in 10 ml of THF, cooled to −78° C. and treated dropwise with 1.8 ml of a 1.6 molar solution of butyl lithium in hexane. After stirring at −78° C. for 1 hour and at room temperature for 1 hour, the reaction mixture was poured on ice/saturated aqueous ammonium chloride solution and extracted with hexane. The organic phase was dried ($Na_2SO_4$) and the solvent evaporated to yield 0.4 g of 2-ethynyl-4,4,7,7-tetramethyl-2-pentyl-2,3,4,5,6,7-hexahydro-1H-indene as yellowish oil.

A reaction flask was filled sequentially with 456 mg of methyl-4-iodo-benzoate, 10 ml of DMF, 1 ml of triethylamine, 48 mg of bis(triphenylphosphine) palladium (II) dichloride and 26 mg of cuprous iodide. The flask was evacuated twice and refilled with argon. The reaction mixture was treated dropwise with a solution of 380 mg of the above mentioned acetylene derivative in 5 ml of DMF. After stirring for 2 hours at room temperature, the reaction mixture was poured on ice/saturated aqueous $NH_4Cl$ solution and extracted with ether. The organic phase was dried, the solvent evaporated and the crude residue was purified with flash chromatography (silica gel, hexane/ethyl acetate 5%) to yield 0.4 g of 4-(4,4,7,7-tetramethyl-2-pentyl-2,3,4,5,6,7-hexahydro-1H-inden-2-yl-ethynyl)-benzoic acid methyl ester as colorless oil.

0.4 g of this methyl ester were dissolved in 10 ml of ethanol and treated with a solution of 0.55 g of KOH in 2 ml of water. After 2 hours at 40° C. the reaction mixture was poured onto ice/water, acidified with 2N HCl and extracted with ether. The organic phase was dried ($Na_2SO_4$) and the solvent evaporated. The crystalline residue was recrystallized from pentane to yield 240 mg of 4-(4,4,7,7-tetramethyl-2-pentyl-2,3,4,5,6,7-hexahydro-1H-inden-2-ethynyl)-benzoic acid as white crystals, m.p. 140–141° C.

EXAMPLE 9

Preparation of (2E, 4E, 6E)-3-methyl-7-(4,4,7,7-tetramethyl-2-pentyl-2,3,4,5,6,7-hexahydro-1H-inden-2-yl)-hepta-2,4,6-trienoic acid

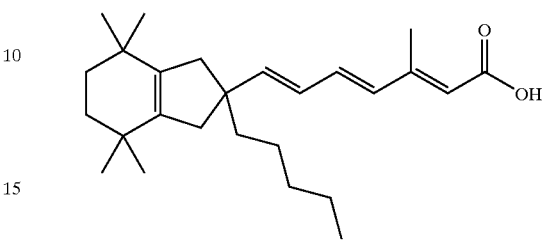

and the (2Z)-isomer

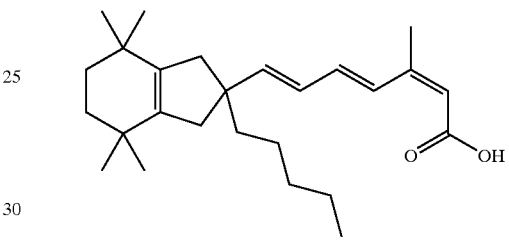

680 mg of 6-(diethoxyphosphoryl)-3-methyl-hexa-2,4-dienoic acid ethyl ester were dissolved in 10 ml of THF and treated dropwise with 2.25 ml of a 1 molar solution of lithium bis(trimethylsilyl)amide in hexane at −78° C. After 10 minutes of stirring, a solution of 500 mg of 4,4,7,7-tetramethyl-2-pentyl-2,3,4,5,6,7-hexahydro-1H-indene-2-carbaldehyde in 5 ml of THF was added dropwise at −78° C. The reaction mixture was slowly warmed to −40° C. and kept at this temperature for 3 hours. The cold reaction mixture was poured in ice/water, acidified with 1 N HCl and extracted with ether. The organic phase was washed with water, dried ($Na_2SO_4$) and the solvent was evaporated. The crude oil was purified with medium pressure chromatography (silica gel, hexane/tert.-butyl methyl ether 1%) to give 250 mg of pure (2Z, 4E, 6E)-3-methyl-7-(4,4,7,7-tetramethyl-2-pentyl-2,3,4,5,6,7-hexahydro-1H-inden-2-yl)-hepta-2,4,6-trienoic acid ethyl ester and 400 mg of (2E, 4E, 6E)-3-methyl-7-(4,4,7,7-tetramethyl-2-pentyl-2,3,4,5,6,7-hexahydro-1H-inden-2-yl)-hepta-2,4,6-trienoic acid ethyl ester as colorless oils.

The two esters were hydrolyzed separately using ethanol/water/potassium hydroxide in analogy to the procedure given in Example 8. After recrystallisation from pentane/ethyl acetate, pure (2Z, 4E, 6E)-3-methyl-7-(4,4,7,7-tetramethyl-2-pentyl-2,3,4,5,6,7-hexahydro-1H-inden-2-yl)-hepta-2,4,6-trienoic acid, m.p. 141–142° C., and (2E, 4E, 6E)-3-methyl-7-(4,4,7,7-tetramethyl-2-pentyl-2,3,4,5,6,7-hexahydro-1H-inden-2-yl)-hepta-2,4,6-trienoic acid, m.p.125–126° C., as colorless crystals were obtained.

EXAMPLE 10

Preparation of 4-(4,4,7,7-tetramethyl-2,3,4,5,6,7-hexahydro-1H-inden-2-ylcarbonylamino)-benzoic acid

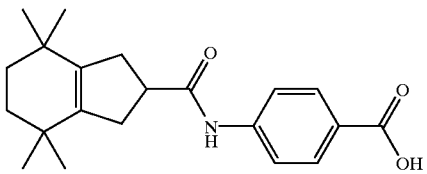

500 mg of 4,4,7,7-tetramethyl-2,3,4,5,6,7-hexahydro-1H-indene-2-carboxylic acid were dissolved in 17 ml of methylene chloride and treated at 0° C. sequentially with 413 mg of 4-amino-benzoic acid ethyl ester dissolved in 2 ml of $CH_2Cl_2$, 27 mg of 4-dimethylamino-pyridine and 515 mg of 1,3-dicyclohexylcarbodiimide. The reaction mixture was stirred at 0° C. for 2 hours and at room temperature for 2 hours, then poured on ice/water and extracted with ethyl acetate. The organic phase was dried ($Na_2SO_4$) and the solvent was evaporated. The semi-crystalline residue was diluted with ether, filtered, the filtrate evaporated. The residue was further purified with medium pressure chromatography (silica gel, hexane/ethyl acetate=4:1) to yield, after crystallization from ethyl acetate, 370 mg of 4-(4,4,7,7-tetramethyl-2,3,4,5,6,7-hexahydro-1H-inden-2-ylcarbonylamino)-benzoic acid ethyl ester as white crystals, m.p. 154–155° C.

320 mg of this ester were hydrolyzed using ethanol/water/THF/KOH in analogy to the procedure given in example 8 and gave after crystallization from ethyl acetate pure 4-(4,4,7,7-tetramethyl-2,3,4,5,6,7-hexahydro-1H-inden-2-ylcarbonylamino)-benzoic acid as white crystals, m.p. 261–262° C.

EXAMPLE 11

Preparation of 4-[(4,4,7,7-tetramethyl-4,5,6,7-tetrahydro-1H-indene-2-carbonyl)-amino]-benzoic acid

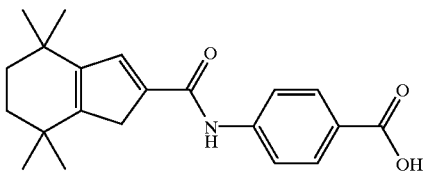

A solution of 2.5 g of 4,4,7,7-tetramethyl-4,5,6,7-tetrahydro-1H-indene-2-carboxylic acid ethyl ester in 10 ml of THF was slowly added at −78° C. to 1.2 equivalent of lithium diisopropylamide in THF (prepared in the usual way from diisopropylamine and n-butyl lithium). After 2 hours of stirring at −78° C. 1.8 g of hexamethylphos-phoramide were added, followed by slow addition of a solution of 3 g of phenylselenyl bromide in 10 ml of THF. The reaction mixture was warmed to 0° C. for 1 hour and then sequentially treated with 6.5 ml of water, 1.3 ml of acetic acid and 6 g of hydrogen peroxide 30%. After 0.5 hour at room temperature, the reaction mixture was poured on a cold, saturated sodium bicarbonate solution, extracted with ether. The organic phase was washed with sodium bicarbonate solution and water, dried over $MgSO_4$, filtrated and the solvent evaporated. The crude product was filtered through a pad of silica gel (hexane/ether 5%) and further purified with medium pressure chromatography (silica gel, hexane/ethyl acetate 3%) to give after recrystallisation from hexane 1.8 g of 4,4,7,7-tetramethyl-4,5,6,7-tetrahydro-1H-indene-2-carboxylic acid ethyl ester as white crystals, m.p. 75–76° C.

1.7 g of this ester were hydrolyzed using ethanol/THF/KOH/water in analogy to the procedure given in example 8 and yielded after recrystallisation from hexane 1.2 g of 4,4,7,7-tetramethyl-4,5,6,7-tetrahydro-1H-indene-2-carboxylic acid as white crystals, m.p. 179–180° C.

1.1 g of this acid were dissolved in 30 ml of methylene chloride and treated successively with 1 g of 4-amino-benzoic acid ethyl ester dissolved in 30 ml of methylene chloride, 60 mg of 4-dimethylamino-pyridine and 1.1 g of 1,3-dicyclohexylcarbodiimide at 0° C. After 6 hours of stirring at room temperature the reaction mixture was poured on ice/saturated ammonium chloride solution and extracted with ethyl acetate. The orange, semi-crystalline residue which resulted after drying ($Na_2SO_4$) and evaporation of the organic solvent, was diluted with ether, filtered, the filtrate evaporated and the residue purified with medium pressure chromatography (silica gel, hexane/ethyl acetate=3:2) to yield after crystallization from hexane/ethyl acetate 1.3 g of 4-[4,4,7,7-tetramethyl-4,5,6,7-tetrahydro-1H-indene-2-carbonyl)-amino]-benzoic acid ethyl ester as beige crystals, m.p. 212–213° C.

This ester was hydrolyzed using 10 equivalents of KOH in ethanol/water/THF at room temperature in analogy to the procedure given in example 8 and yielded after crystallization from ethyl acetate 4-[4,4,7,7-tetramethyl-4,5,6,7-tetrahydro-1H-indene-2-carbonyl)-amino]-benzoic acid ethyl ester as white crystals, m.p.272–274° C.

EXAMPLE 12

Effects of RAR Selective Retinoids on Repair of Alveoli in Elastase-induced Emphysema RAR selective agonists were evaluated for its effects on alveolar repair in the rat model of elastase-induced emphysema in rats (D. Massaro et al. *Nature Medicine* (1997, 3, 675). Animals were divided into treatment groups of approximately eight. Lung inflammation and alveolar damage was induced in male Sprague Dawley rats by a single instillation of pancreatic elastase(porcine derived, Calbiochem) 2 U/gram body mass. Three weeks post injury all-trans retinoic acid or RAR agonist was dissolved in dimethylsulfoxide (20 mg/ml) and stored at −20° C. Fresh working stocks were prepared fresh daily by dilution in PBS to a final concentration of 2 mg/ml. Animals were dosed once daily with the retinoid by intraperitoneal injection or orally, starting 21 days post injury. Control groups were challenged with elastase and 21 days later treated with Vehicle (DMSO/PBS) for 14 days. Animals were sacrificed 24 hours after the last dose of by exsanguination under deep anesthesia.

The lungs were inflated with 10% neutral buffered formalin by intratracheal instillation at a constant rate (1 ml/gram body mass/min). The lung was excised and immersed in fixative for 24 hours prior to processing. Standard methods were used to prepare 5 um paraffin sections. Sections were stained with Hematoxylin and Eosin (H% E). Computerized Morphometric analysis was performed to determine the average alveolar size and alveolar number (Table 1).

TABLE 1

| Dose [mg/kg] | | % repair area | |
|---|---|---|---|
| 0.5 | i.p. | 54 | compound D |
| 0.3 | p.o. | 11.1 | compound D |

TABLE 1-continued

| Dose [mg/kg] | | % repair area | |
|---|---|---|---|
| 1 | p.o. | 44 | compound D |
| 3 | p.o. | 48.6 | compound D | i.p. intraperitoneal
p.o. per os

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application, including but not limited to European Patent Application No. 99115223.2, filed Aug. 2, 1999, are hereby incorporated by reference in their entirety for all purposes to the same extent as if each individual patent, patent application or publication were so individually denoted.

What is claimed is:

1. A retinoid, wherein the retinoid is a compound of formula I

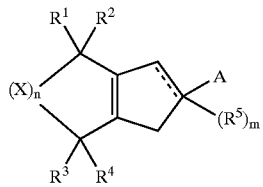

wherein
the dotted bond is either present and forms a double bond, or is absent;
$R^1$, $R^2$, $R^3$, $R^4$ are independently of each other hydrogen or alkyl;
n is 1, 2 or 3;
X is $R^8R^9C<$ for n=1, 2 or 3; or
X is oxygen for n=1;
each $R^8$ and each $R^9$ is independently hydrogen or alkyl;
$R^5$ is hydrogen, alkyl, alkoxy, alkoxy-alkyl-, alkylthio, alkyl-$NR^{10}$—, alkenyl, alkenyloxy, alkynyl, benzyl, cycloalkyl-alkyl, or phenyl-alkyl;
$R^{10}$ is hydrogen or alkyl;
m is 0 when the dotted bond is present; and
m is 1 when the dotted bond is absent; and
A is a residue of formula

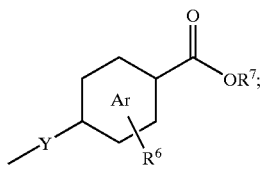

wherein
Ar surrounded by hexagon shown above is a heteroarylic ring having at least three ring carbon atoms and is bonded to each of Y, $R^6$ and —C(O)$OR^7$ via a different ring carbon atom;
$R^6$ is hydrogen, halogen, alkoxy or hydroxy;
$R^7$ is hydrogen or alkyl; and
Y —COO—, —OCO—, —CONR$^{10}$—, —NR$^{10}$CO—, —CH=CH—, —C≡C—, —COCH=CH—, —CHOHCH=CH—, —CH$_2$O—, —CH$_2$S—, —CH$_2$SO—, —CH$_2$SO$_2$—, —CH$_2$NR$^{10}$—, —OCH$_2$—, —SCH$_2$—, —SOCH$_2$—, —SO$_2$CH$_2$— or —NR$^{10}$CH$_2$—, oriented so that Y is bonded to the Ar surrounded by hexagon via the portion of Y written to the right above, with the proviso that when Y is —OCO—, —NR$^{10}$CO—, —OCH$_2$—, —SCH$_2$—, —SOCH$_2$—, —SO$_2$CH$_2$— or —NR$^{10}$CH$_2$—, $R^5$ is hydrogen, alkyl, alkoxy-alkyl-, alkenyl, alkynyl, benzyl, cycloalkyl-alkyl or phenyl-alkyl;
or a pharmaceutically active salt of the compound.

2. The retinoid according to claim 1, wherein $R^8$ and $R^9$ are the same.

3. The retinoid according to claim 2, wherein each $R^8$ is hydrogen and each $R^9$ is hydrogen.

4. The retinoid according to claim 1, wherein the retinoid is a compound of formula

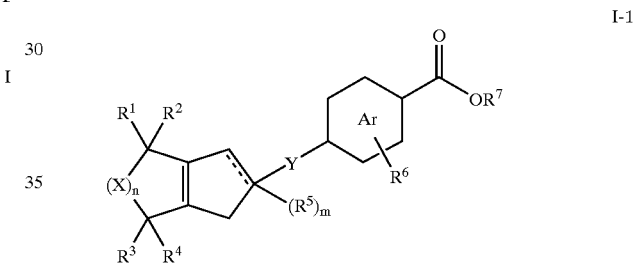

wherein
the dotted bond is present and forms a double bond, or is absent;
$R^1$, $R^2$, $R^3$, $R^4$ are independently of each other hydrogen or alkyl;
n is 1, 2 or 3;
X is $R^8R^9C<$ for n=1, 2 or 3; or
X is oxygen for n=1;
$R^5$ is hydrogen, alkyl, alkoxy, alkenyl, alkenyloxy, alkynyl, benzyl, cycloalkyl-alkyl or phenylalkyl;
m is 0 when the dotted bond is present; or
m is 1 when the dotted bond is absent;
Ar surrounded by hexagon shown above is a heteroarylic ring having at least three ring carbon atoms and is bonded to each of Y, $R^6$ and —C(O)$OR^7$ via a different ring carbon atom;
$R^6$ is hydrogen, halogen, alkoxy or hydroxy;
$R^7$ is hydrogen or alkyl;
Each $R^8$ and each $R^9$ is independently hydrogen or alkyl; and
Y —COO—, —OCO—, —CONH—, —NHCO—, —CH=CH—, —C≡C—, —COCH=CH—, —CHOHCH=CH—, —CH$_2$O—, —CH$_2$S— or —CH$_2$NH— oriented so that Y is bonded to the Ar surrounded by hexagon via the portion of Y written to the right above; with the proviso that when Y is —OCO— or —NHCO—, R⁵ is hydrogen, alkyl, alkenyl, alkynyl, benzyl, cycloalkyl-alkyl or phenylalkyl;

or when $R^7$ is hydrogen, a pharmaceutically active salt of the compound.

5. The retinoid according to claim 4, wherein $R^8$ and $R^9$ are the same.

6. The retinoid according to claim 5, wherein each $R^8$ is hydrogen and each $R^9$ is hydrogen.

7. The retinoid according to claim 4, wherein the compound has the formula

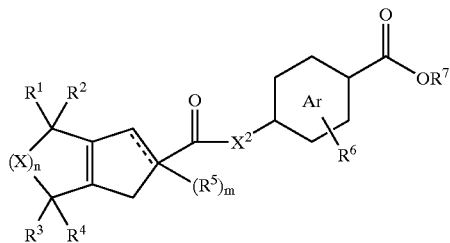

IA wherein $X^2$ is oxygen or —NH—.

8. The retinoid according to claim 7, wherein $X^2$ is oxygen and n is 2.

9. The retinoid according to claim 7, wherein Ar is pyridine.

10. The retinoid according to claim 9, wherein the compound is 6-[(4,4,7,7-tetramethyl-2-pentyl-2,3,4,5,6,7-hexahydro-1H-indene-2-carbonyl)-amino]-nicotinic acid.

11. The retinoid according to claim 4, wherein the compound has the formula

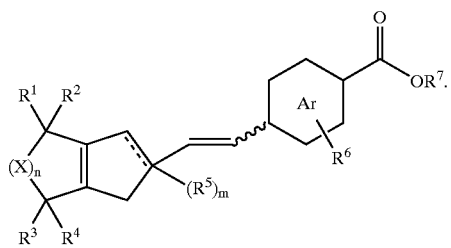

IB

12. The retinoid according to claim 4, wherein the compound has the formula

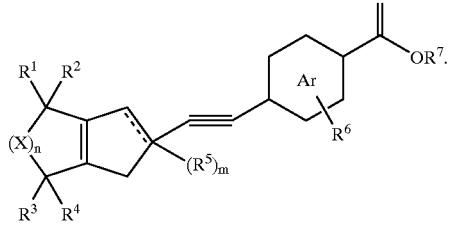

IC

13. The pharmaceutically active salt of the retinoid according to claim 1, which is a pharmaceutically acceptable salt of the retinoid formed from a pharmaceutically acceptable base.

* * * * *